(12) United States Patent
Moeller et al.

(10) Patent No.: US 8,846,335 B2
(45) Date of Patent: Sep. 30, 2014

(54) DEVICE FOR RAPIDLY DETECTING MICROORGANISMS

(75) Inventors: Stephanie J. Moeller, Stillwater, MN (US); Jimmie R. Baran, Jr., Prescott, WI (US); Jesse D. Miller, Hudson, WI (US); Neil Percy, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/703,149

(22) PCT Filed: Jun. 27, 2011

(86) PCT No.: PCT/US2011/041943
§ 371 (c)(1),
(2), (4) Date: Dec. 10, 2012

(87) PCT Pub. No.: WO2012/012106
PCT Pub. Date: Jan. 26, 2012

(65) Prior Publication Data
US 2013/0089923 A1    Apr. 11, 2013

Related U.S. Application Data

(60) Provisional application No. 61/359,933, filed on Jun. 30, 2010.

(51) Int. Cl.
| C12Q 1/08 | (2006.01) |
| C12N 11/04 | (2006.01) |
| C12Q 1/06 | (2006.01) |
| C12M 1/00 | (2006.01) |
| B82Y 5/00 | (2011.01) |

(52) U.S. Cl.
CPC ............... *C12M 23/22* (2013.01); *C12Q 1/06* (2013.01); *B82Y 5/00* (2013.01)
USPC .......................................... 435/34; 435/182

(58) Field of Classification Search
None
See application file for complete search history.

(56) References Cited

U.S. PATENT DOCUMENTS

| 2,801,185 | A | 7/1957 | Iler |
| 4,522,958 | A | 6/1985 | Das |
| 4,565,783 | A | 1/1986 | Hansen |
| 5,037,579 | A | 8/1991 | Matchett |
| 5,089,413 | A | 2/1992 | Nelson |
| 5,232,838 | A | 8/1993 | Nelson |
| 5,364,766 | A | 11/1994 | Mach |
| 5,443,963 | A | 8/1995 | Lund |
| 5,462,860 | A | 10/1995 | Mach |
| 5,601,998 | A | 2/1997 | Mach |
| 5,635,367 | A | 6/1997 | Lund |
| 5,681,712 | A | 10/1997 | Nelson |
| 5,891,376 | A * | 4/1999 | Christie et al. ................. 264/234 |
| 5,994,440 | A | 11/1999 | Staples |
| 6,586,483 | B2 | 7/2003 | Kolb |
| 7,037,708 | B1 | 5/2006 | Runge |
| 7,371,464 | B2 | 5/2008 | Sherman |
| 7,695,818 | B2 | 4/2010 | Sherman |
| 2004/0067247 | A1 * | 4/2004 | De Sloovere et al. ......... 424/409 |
| 2005/0065237 | A1 | 3/2005 | Schmidt |
| 2006/0204755 | A1 | 9/2006 | Torii |
| 2008/0226898 | A1 | 9/2008 | Schmidt |
| 2010/0159499 | A1 | 6/2010 | Baker |

FOREIGN PATENT DOCUMENTS

| WO | WO 00/06495 | 2/2000 |
| WO | WO 2010/022111 | 2/2010 |

OTHER PUBLICATIONS

World Wide Metric.Datasheet [online].World Wide Metric, Inc. Copyright 2013 [retrieved Oct. 18, 2013]. Retrieved from the Internet: <URL: http://www.worldwidemetric.com/measurements.html>.*
3M Petrifilm™ Coliform Count Plate, Interpretation Guide, 1999, St. Paul, MN, USA, pp. 1-5.

* cited by examiner

*Primary Examiner* — John S Brusca
*Assistant Examiner* — Sharon M Papciak

(57) ABSTRACT

The disclosure includes: a coating composition, comprising a powdered cold-water-soluble gelling agent and surface-modified nanoparticles disposed in the powdered cold-water-soluble gelling agent; a coated film that includes a transparent film coated with the coating composition; and a device for growing microorganisms, including the coated film releasably attached to at least a portion of a body member that includes a self-supporting and water-proof substrate.

12 Claims, 2 Drawing Sheets

DEVICE FOR RAPIDLY DETECTING MICROORGANISMS

FIELD OF THE DISCLOSURE

The disclosure relates to devices useful for the growing and detection of microorganisms, and coated films and coating compositions useful in the preparation of devices for the growing and detection of microorganisms, where the coatings include surface-modified nanoparticles.

BACKGROUND

Rapid detection of microorganisms has been facilitated by the use of various types of microbial culture growth devices, including a thin film culture card device that permits visual observation of culture colonies on the inside of the device. Examples of these types of devices include 3M PETRIFILM thin film culture card devices.

SUMMARY

There is a need for rapid detection of microorganisms. It will be appreciated that factors involved in rapid detection of microorganisms can include the transparency of devices through which a visual (or imaged) determination of the presence or absence of a microorganism in a sample is made. As described in the present disclosure, the inclusion of surface-modified nanoparticles in powdered coatings on transparent films in microbial culture growth devices can enhance rapid detection of the presence or absence of a microorganism in a sample suspected of including a microorganism.

In one aspect, the present disclosure provides a coating composition useful for enhancing the detection of microorganisms in culture devices, the coating composition including a powdered cold-water-soluble gelling agent, and surface-modified nanoparticles dispersed in the powdered cold-water-soluble gelling agent in a range from 0.00001 wt. % to about 0.1 wt. % of the coating composition, the surface-modified nanoparticles having an average particle diameter of less than about 100 nanometers. In some embodiments of the coating composition, the surface-modified nanoparticles are included in a range from 0.0001 wt. % to 0.01 wt. % of the coating composition.

In some embodiments of the coating composition, the surface-modified nanoparticles have an average primary particle diameter less than about 50 nanometers, or less than about 20 nanometers, or in a range from about 3 nanometers to about 20 nanometers, or in a range from about 3 nanometers to about 10 nanometers. In some embodiments, the surface-modified nanoparticles have an average primary particle diameter less than 50 nanometers, or even less than 20 nanometers. In some embodiments, the surface-modified nanoparticles have an average primary particle diameter in a range from 3 nanometers to 20 nanometers, or even in a range from 3 nanometers to 10 nanometers.

In some embodiments of the coating composition, the surface-modified nanoparticles include nanoparticles selected from the group including silica, titania, alumina, zirconia, vanadia, ceria, iron oxide, antimony oxide, tin oxide, calcium phosphate, hydroxyapatite, aluminum/silica and combinations thereof.

In some embodiments of the coating composition, the surface-modified nanoparticles include surface groups selected from the group including hydrophobic groups, hydrophilic groups and combinations thereof. In some embodiments, the surface groups are derived from an agent selected from the group including silane groups, organic acid groups, organic base groups and combinations thereof.

In some embodiments of the coating composition, the powdered cold-water-soluble gelling agent comprises a mixture of locust bean gum and xanthan gum. In some embodiments, the locust bean gum and xanthan gum are present in a ratio of about 1:1.

In another aspect, the present disclosure provides a coated film, including a transparent film having an adhesive layer on a major surface thereof, where the adhesive is non-inhibitory to the growth of microorganisms; and further including a coating composition adhered to the adhesive layer, where the coating composition includes a powdered cold-water-soluble gelling agent, and surface-modified nanoparticles dispersed in the powdered cold-water-soluble gelling agent in a range from 0.00001 wt. % to about 0.1 wt. % of the coating composition, the surface-modified nanoparticles having an average primary particle diameter of less than about 100 nanometers.

In some embodiments of the coated film, the transparent film is selected from the group including polyester, polyethylene, polypropylene, polystyrene and silicone. In some embodiments of the coated film, the transparent film is biaxially oriented polypropylene. In some embodiments of the coated film, the transparent film has a thickness in a range from about 2 micrometers to about 38 micrometers.

In some embodiments of the coated film, the adhesive is a pressure-sensitive adhesive. In some embodiments of the coated film, the adhesive is substantially transparent when wetted with water.

In another aspect, the current description includes a device for growing microorganisms, including: (a) a body member including a substrate having upper and lower surfaces, wherein the substrate is self-supporting and water-proof; (b) a layer of adhesive coated on the upper surface of the substrate, wherein the adhesive is non-inhibitory to the growth of microorganisms; (c) a cold-water-soluble powder adhered uniformly to the layer of adhesive, the cold-water-soluble powder comprising at least a single ingredient selected from the group consisting of gelling agent, one or more nutrients for growing microorganisms, and a mixture thereof; and (d) a cover sheet comprising a transparent film having an adhesive layer on a major surface thereof, where the adhesive is non-inhibitory to the growth of microorganisms; and further including a coating composition adhered to the adhesive layer, where the coating composition includes a powdered cold-water-soluble gelling agent, and surface-modified nanoparticles dispersed in the powdered cold-water-soluble gelling agent, wherein the coated surface of the cover sheet faces the upper surface of the substrate, and wherein the cover sheet is releasably adhered to at least a portion of the body member.

In some embodiments, the device of the current description includes a hydrophobic spacer element adhered to the upper surface of the substrate, forming side walls to retain a predetermined amount of liquid in contact with the substrate. In some embodiments, the hydrophobic spacer element comprises a hydrophobic foam sheet defining an aperture therein. In some embodiments, the hydrophobic sheet comprises polystyrene or polyethylene.

In some embodiments of the device of the current description, the substrate is a film selected from the group including polyester, polyethylene, polypropylene, and polystyrene. In some embodiments, the film has a thickness in a range from about 2 micrometers to about 38 micrometers. In some embodiments of the device of the current description, the substrate has a grid pattern printed thereon.

In some embodiments of the device of the current description, the gelling agent included in the coating composition is selected from the group including xanthan gum, guar gum, carboxymethyl cellulose, hydroxyethyl cellulose, and algin. In some embodiments, the gelling agent is guar gum, xanthan gum, or mixtures thereof.

In some embodiments of the device of the current description, the adhesive layer on a major surface of the transparent film includes a pressure-sensitive adhesive. In some embodiments, the adhesive layer on a major surface of the transparent film is substantially transparent when wetted with water.

GLOSSARY

"Cold-water-soluble" refers to material which forms a solution in water at room temperature (i.e., about 25° C.).

"Opaque" refers to a substrate having at most 10% light transmission.

"Primary particle diameter" and "particle size" refer to the maximum cross-sectional dimension of a particle. If the particle is present in the form of an aggregate, the terms "primary particle diameter" and "particle size" refer to the maximum cross-sectional dimension of the aggregate.

"Powder" refers to a finely divided particulate material having an average diameter in a range from 0.1 micrometer up to 400 micrometers.

"Surface-modified nanoparticle" refers to a particle that includes surface groups attached to the surface of the particle. The surface groups modify the character of the particle.

"Transparent" refers to a substrate having at least 90% light transmission.

Like reference numbers in the various figures indicate like elements. However, it will be understood that the use of a number to refer to a component in a given figure is not intended to limit the component in another figure labeled with the same number. Some elements may be present in identical or equivalent multiples; in such cases only one or more representative elements may be designated by a reference number but it will be understood that such reference numbers apply to all such identical elements. Unless otherwise indicated, all figures and drawings in this document are not to scale and are chosen for the purpose of illustrating different embodiments of the description. In particular the dimensions of the various components are depicted in illustrative terms only, and no relationship between the dimensions of the various components should be inferred from the drawings, unless so indicated. Although terms such as "top", bottom", "upper", "lower", "under", "over", "front", "back", "outward", "inward", "up" and "down", and "first" and "second" may be used in this disclosure, it should be understood that those terms are used in their relative sense only unless otherwise noted. In particular, in some embodiments certain components may be present in interchangeable and/or identical multiples (e.g., pairs). For these components, the designation of "first" and "second" may apply to the order of use, as noted herein (with it being irrelevant as to which one of the components is selected to be used first).

DETAILED DESCRIPTION

Figure 1:
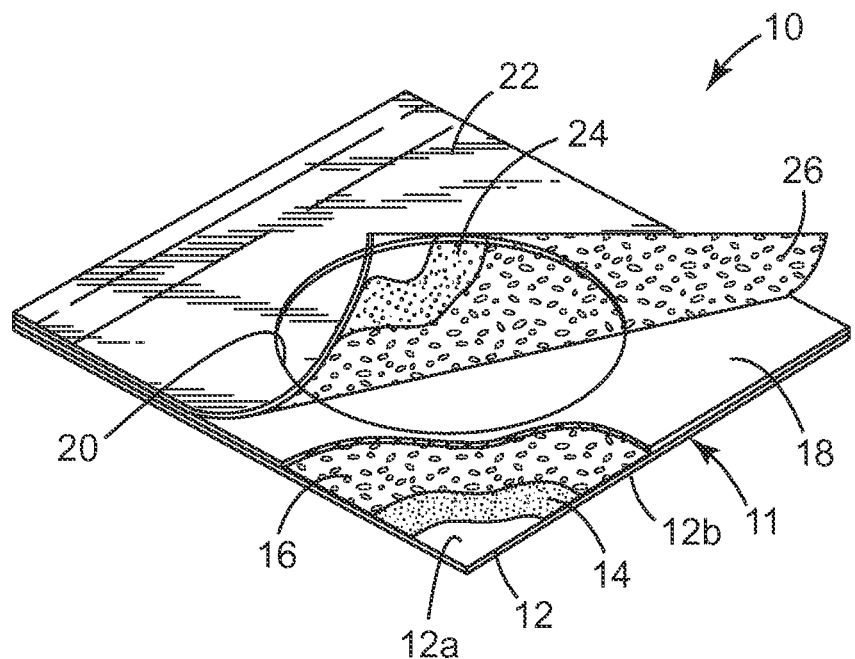
FIG. 1 is a top perspective view, partially in section, of an exemplary embodiment of a microbiological growing device.
Figure 4:
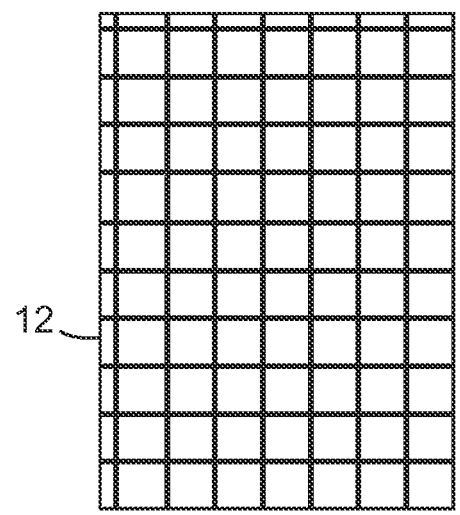
FIG. 4 is a top view of the device of FIG. 2 showing a grid pattern printed on the substrate.

FIG. 1 illustrates an exemplary embodiment of device for growing microorganisms. Device 10 includes body member 11 comprising self-supporting water-proof substrate 12 having upper surface 12a and lower surface 12b. In some embodiments, substrate 12 is a relatively stiff film of a material such as polyester, polypropylene or polystyrene which will not absorb or otherwise be affected by water. Polyester films having a thickness from about 100 micrometers to about 178 micrometers, and polypropylene films having a thickness from about 100 micrometers to about 200 micrometers, as well as polystyrene films having a thickness of about 380 micrometers have each been found to be suitable for substrate 12. Other suitable substrates include paper with a polyethylene or other water-proof coating. An example of a suitable polyethylene-coated paper substrate is "Schoeller Type MIL" photoprint paper (commercially available from Schoeller Pulaski, New York). Substrate 12 may be either transparent or opaque, depending on whether one wishes to view bacterial colonies through the substrate. In the exemplary embodiment shown in FIG. 4, substrate 12 has a square grid pattern printed on lower surface 12b to facilitate the counting of bacterial colonies.

Upper surface 12a has layer of adhesive 14 which holds a dry gelling agent and/or nutrients in a uniform layer for easy hydration. Layer of adhesive 14 is water-insoluble and non-inhibitory to the growth of microorganisms. In some embodiments, adhesive 14 is sufficiently transparent when wet to enable the viewing of bacterial colonies through the film coated with the adhesive. In some embodiments, adhesive 14 is a pressure-sensitive adhesive. In some other embodiments, heat-activated adhesives wherein a lower melting substance is coated onto a higher melting substance may also be used. Water-activated adhesives such as mucilage may also be useful.

Adhesive 14 is typically coated onto substrate 12 in a thickness which is less than the diameter of the particles of the powdered gelling agent and/or nutrients, in order to adhere the particles of powder 16 to the substrate without completely embedding the particles in the adhesive. A uniform layer of powder 16 is desired with sufficient surface area exposed for hydration. Typically, an adhesive layer in the thickness range from about 5 micrometers to about 13 micrometers is suitable.

Suitable adhesives are transparent when wetted with water. Examples of suitable adhesives include a copolymer of isooctylacrylate/acrylamide in a mole ratio of 94:6. Other pressure sensitive adhesives which may be used include isooctylacrylate/acrylic acid in a mole ratio of 95:5 or 94:6, and silicone rubber.

A layer of cold-water-soluble powder 16 is adhered uniformly to adhesive layer 14. Cold-water-soluble powder 16 includes at least one ingredient selected from the group consisting of a gelling agent, one or more nutrients for growing microorganisms, and a mixture of a gelling agent and one or more nutrients for growing microorganisms.

The cold-water-solubility of the powders employed in the devices of the present disclosure may result, for example, from the inclusion in these powders of an appropriate gelling agent. Suitable gelling agents for inclusion in cold-water-soluble powder 16 include both natural and synthetic gelling agents which form solutions in water at room temperature. Gelling agents such as hydroxyethyl cellulose, carboxymethyl cellulose, polyacrylamide, locust bean gum and algin form solutions in water at room temperature and are suitable gelling agents for providing powders which are cold-water-soluble. In some embodiments the gelling agents for cold-water-soluble powder 16 are guar gum and xanthan gum, these gelling agents being useful individually or in combination with one another.

In some embodiments, cold-water-soluble powder 16 may comprise only a gelling agent. Where the device, as manufactured, contains a powder comprising only a gelling agent, the end user typically adds special nutrients tailored to the type of microorganisms to be grown. For example, dry powdered nutrients may be suspended in a rapidly-evaporating liquid such as ethanol. In other instances, dry powdered nutrients may be suspended or dissolved in aqueous solutions. An aliquot of the liquid is added to the surface of substrate 12 which has been coated previously with adhesive and gelling agent. The liquid is then allowed to evaporate, leaving ample nutrients along with the gelling agent.

In another embodiment, cold-water-soluble powder 16 may comprise nutrients but no gelling agent. In many microbiological tests, such as tests for bacteria identification or antibiotic susceptibility, broth media are used, and there is no need for a viscous gel. In devices for carrying out such tests, the gelling agent may be omitted. Nutrients suitable for growing microorganisms in the current device form solutions in water at room temperature.

Optionally, cold-water-soluble powder 16 may further comprise a selective agent, a detection reagent, or a combination of these.

Non-limiting examples of suitable gelling agents, nutrients and mixtures thereof for supporting growth of microorganisms in a device of the present disclosure include those described in U.S. Pat. Nos. 4,565,783; 5,089,413; 5,232,838; 5,364,766; 5,443,963; 5,462,860; 5,601,998; 5,635,367; and 5,681,712; the descriptions of each of which are incorporated herein by reference; these references also include non-limiting examples of selective agents and detection reagents.

In the exemplary embodiment shown in FIG. 1, body member 11 includes hydrophobic spacer element 18 applied to upper surface 12a of substrate 12, hydrophobic spacer element 18 having circular aperture 20 cut through its center to expose cold-water-soluble powder 16 on substrate 12. The walls of aperture 20 provide a well of predetermined size and shape to confine the medium following hydration. Hydrophobic spacer element 18 is thick enough to form a well of a desired volume (e.g., 1 milliliter, 2 milliliters, or 3 even milliliters). Closed cell polyethylene foam is typically used for hydrophobic spacer element 18, but any material which is hydrophobic (i.e., non-wetting), inert to microorganisms, and capable of withstanding sterilization may be used.

Referring again to FIG. 1, cover sheet 22 is releasably adhered to one edge of the upper surface of hydrophobic spacer element 18. In the present disclosure, cover sheet 22 is selected to be transparent, in order to facilitate counting of microbial colonies, and is typically selected to be impermeable to bacteria and water vapor (i.e., cover sheet 22 prevents undesired contamination of the dehydrated medium during shipping, storage and use of the devices and provides an environment which will support the growth of microorganisms during the incubation period). In some embodiments, cover sheet 22 has same properties (e.g., stiffness) as substrate 12, but need not be as stiff. Cover sheet 22 can be selected to provide the amount of oxygen transmission necessary for the type of microorganism desired to be grown. For example, some polyester films have low oxygen permeability (less than 5 g/645 $cm^2$/24 hours per 25 micrometers of thickness) and would be suitable for growing anaerobic bacteria. On the other hand, some polyethylenes have high oxygen permeability (e.g., approximately 500 g/645 $cm^2$/24 hours per 25 micrometers of thickness) and would be suitable for aerobic organisms. Suitable material for cover sheet 22 includes biaxially-oriented polypropylene film, which in some exemplary embodiments has a thickness of about 40 micrometers.

Figure 2:
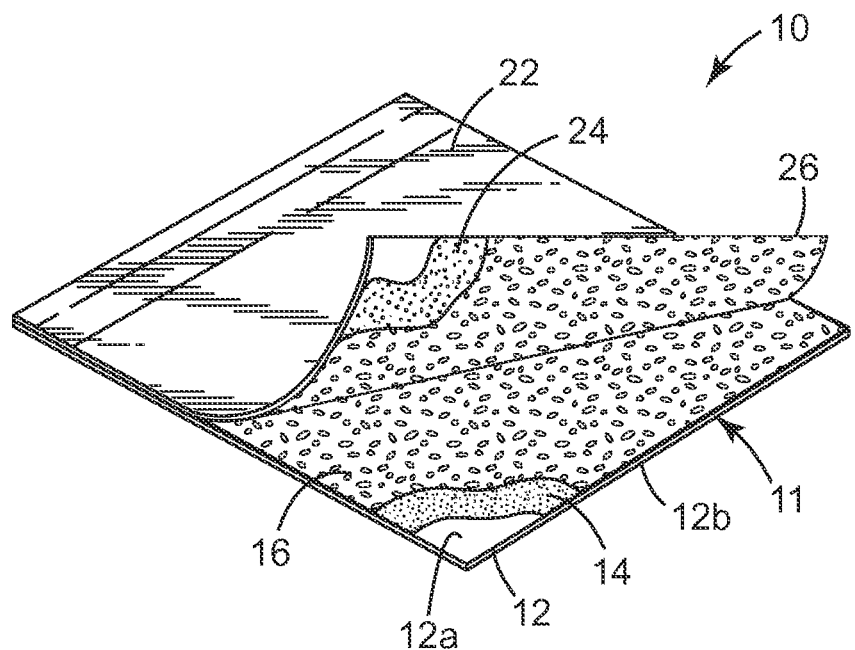
FIG. 2 is a top perspective view, partially in section, of an exemplary embodiment of a microbiological growing device.

In the exemplary embodiment illustrated in FIG. 2, cover sheet 22 may be releasably adhered to one edge of substrate 12. In the exemplary embodiment of FIG. 2, hydrophobic spacer element 18 is not present. A template, such as a weighted circular ring, may be applied temporarily to the outside of cover sheet 22, after closing, to confine the hydration of materials by an aqueous sample to a specific region.

In FIG. 1, cover sheet 22 is coated on a major surface thereof with layer of adhesive 24 and layer of a coating composition 26. The major surface of cover sheet 22 having layer of coating composition 26 faces upper surface 12a of substrate 12. Layer of adhesive 24 is water-insoluble and non-inhibitory to the growth of microorganisms, and is sufficiently transparent when wet to enable the viewing of gas bubbles or microbial colonies through the film coated with the adhesive. In some embodiments, layer of adhesive 24 comprises a pressure-sensitive adhesive. A uniform layer of coating composition 26 is desired with sufficient surface area exposed for hydration. Typically, layer of adhesive 24 has a thickness in a range from about 5 micrometers to about 13 micrometers.

Suitable adhesives are substantially transparent and when wetted with water, and may include those described in U.S. Pat. Nos. 4,565,783, 5,089,413, 5,681,712, and 5,232,838, the descriptions of each of which are incorporated herein by reference. In some embodiments, examples of suitable adhesives include a copolymer of isooctylacrylate/acrylamide, typically used in a mole ratio of 94:6. In some embodiments, pressure sensitive adhesives which may be used include isooctylacrylate/acrylic acid in a mole ratio of 95:5 or 94:6. In some other embodiments, silicone pressure sensitive adhesives may be used, including for example those described in U.S. Pat. Nos. 7,695,818 and 7,371,464, the descriptions of each of which are incorporated herein by reference.

Layer of coating composition 26 includes surface-modified nanoparticles (e.g., inorganic nanoparticles), having a primary particle diameter of less than 100 nanometers, and typically disposed in a powdered cold-water-soluble gelling agent. The surface-modified nanoparticles have surface groups that modify solubility characteristics of the nanoparticles.

The surface-modified nanoparticles are selected such that the coating composition formed therewith is free from a degree of particle agglomeration or aggregation that would interfere with the desired properties of the coating composition including the ability of the coating composition to minimize formation of air bubbles or other irregularities. The surface-modified nanoparticles are selected to be compatible with the powdered cold-water-soluble gelling agent. For a powdered cold-water-soluble gelling agent that includes a variety of components, the surface-modified nanoparticles may be selected to be compatible with at least one component of the powdered cold-water-soluble gelling agent.

One method of assessing the compatibility of the surface-modified nanoparticles with the powdered cold-water-soluble gelling agent ("gelling agent") includes determining whether the resulting coating composition, when hydrated, forms a transparent hydrogel with minimal formation of air bubbles or other irregularities. One useful method of determining whether a transparent hydrogel is formed includes combining the surface-modified nanoparticles and the gelling agent and observing whether the surface-modified nanoparticles appear to dissolve such that the resulting hydrogel is transparent. The nature of the inorganic particle component of the surface-modified particles will prevent the surface-modified nanoparticles from actually dissolving in the hydrogel, i.e., the surface-modified nanoparticles will be dispersed in the hydrogel. However, the compatibility of the surface groups with the gelling agent will give the surface-modified nanoparticles the appearance of dissolving in the hydrogel. As the size of the surface-modified nanoparticles increases, the haziness of the hydrogel generally increases. Preferred surface-modified nanoparticles are selected such that they do not settle out of the hydrogel.

The surface-modified nanoparticles can also include at least two different surface groups. The surface groups may be selected to provide a statistically averaged, randomly surface-modified particles.

The surface groups are present on the surface of the particle in an amount sufficient to provide surface-modified nanoparticles that are capable of being subsequently dispersed in the gelling agent. The surface-modifying groups preferably are present in an amount sufficient to form a monolayer, preferably a continuous monolayer, on the surface of the particle.

Surface-modifying groups may be derived from surface-modifying agents. Schematically, surface-modifying agents can be represented by the formula A-B, where the A group is capable of attaching to the surface of the particle and the B group is a compatibilizing group that may be reactive or non-reactive with a component of the composition. Compatibilizing groups can be selected to render the nanoparticles relatively more polar, relatively less polar or relatively non-polar.

Suitable classes of surface-modifying agents include, e.g., silanes, organic acids organic bases and alcohols. The selection of treatment agent is determined, in part, by the chemical nature of the metal oxide surface. Silanes are typically selected for silica and other for siliceous fillers. Silanes and carboxylic acids are typically selected for metal oxides such as zirconia. The required amount of surface-modifier is dependant upon several factors such nanoparticle size, particle type, modifier molecular weight, and modifier type. The attachment procedure or reaction conditions required also depend on the surface-modifier used. For silanes it is typical to surface treat at elevated temperatures for from 1 to 24 hr approximately. Surface treatment agents such as carboxylic acids do not require elevated temperatures or extended time.

In some embodiments, useful surface-modifying agents include silanes. Examples of useful silanes include organosilanes including, e.g., alkylchlorosilanes, alkoxysilanes, e.g., methyltrimethoxysilane, methyltriethoxysilane, ethyltrimethoxysilane, ethyltriethoxysilane, n-propyltrimethoxysilane, n-propyltriethoxysilane, i-propyltrimethoxysilane, i-propyltriethoxysilane, butyltrimethoxysilane, butyltriethoxysilane, hexyltrimethoxysilane, octyltrimethoxysilane, 3-mercaptopropyltrimethoxysilane, n-octyltriethoxysilane, phenyltriethoxysilane, polytriethoxysilane, vinyltrimethoxysilane, vinyldimethylethoxysilane, vinylmethyldiacetoxysilane, vinylmethyldiethoxysilane, vinyltriacetoxysilane, vinyltriethoxysilane, vinyltriisopropoxysilane, vinyltrimethoxysilane, vinyltriphenoxysilane, vinyltri(t-butoxy)silane, vinyltris(isobutoxy) silane, vinyltris(isopropenoxy)silane and vinyltris(2-methoxyethoxy)silane; trialkoxyarylsilanes; isooctyltrimethoxy-silane; N-(3-triethoxysilylpropyl)methoxyethoxyethoxy ethyl carbamate; N-(3-triethoxysilylpropyl)methoxyethoxyethoxyethyl carbamate; silane functional (meth)acrylates including, e.g., 3-(methacryloyloxy)propyltrimethoxysilane, 3-acryloyloxypropyltrimethoxysilane, 3-(methacryloyloxy)propyltriethoxysilane, 3-(methacryloyloxy)propylmethyldimethoxysilane, 3-(acryloyloxypropyl)methyldimethoxysilane, 3-(methacryloyloxy)propyldimethylethoxysilane, 3-(methacryloyloxy)methyltriethoxysilane, 3-(methacryloyloxy)methyltrimethoxysilane, 3-(methacryloyloxy)propyldimethylethoxysilane, 3-(methacryloyloxy)propenyltrimethoxysilane and 3-(methacryloyloxy)propyltrimethoxysilane; polydialkylsiloxanes including, e.g., polydimethylsiloxane, arylsilanes including, e.g., substituted and unsubstituted arylsilanes, alkylsilanes including, e.g., substituted and unsubstituted alkyl silanes including, e.g., methoxy and hydroxy substituted alkyl silanes, and combinations thereof.

Useful organic acid surface-modifying agents include oxy-acids of carbon (e.g., carboxylic acids), sulfur- and phosphorus-containing groups, and combinations thereof.

Representative examples of polar surface-modifying agents having carboxylic acid functionality include $CH_3O(CH_2CH_2O)_2CH_2COOH$ (hereafter MEEAA) and 2-(2-methoxyethoxy)acetic acid having the chemical structure $CH_3OCH_2CH_2OCH_2COOH$ (hereafter MEAA) and mono(polyethylene glycol) succinate.

Representative examples of non-polar surface-modifying agents having carboxylic acid functionality include octanoic acid, dodecanoic acid and oleic acid.

Examples of suitable phosphorus containing acids include phosphonic acids including, e.g., octylphosphonic acid, laurylphosphonic acid, decylphosphonic acid, dodecylphosphonic acid and octadecylphosphonic acid.

Useful organic base surface-modifying agents include, e.g., alkylamines including, e.g., octylamine, decylamine, dodecylamine and octadecylamine.

Examples of other useful non-silane surface-modifying agents include acrylic acid, methacrylic acid, beta-carboxyethyl acrylate, mono-2-(methacryloyloxyethyl)succinate, and combinations thereof. A useful surface-modifying agent that imparts both polar character and reactivity to the nanoparticles is mono(methacryloyloxypolyethyleneglycol)succinate.

Examples of suitable surface-modifying alcohols include, e.g., aliphatic alcohols including, e.g., octadecyl, dodecyl, lauryl and furfuryl alcohol, alicyclic alcohols including, e.g., cyclohexanol, and aromatic alcohols including, e.g., phenol and benzyl alcohol, and combinations thereof.

A variety of methods are available for modifying the surface of nanoparticles including, e.g., adding a surface-modifying agent to nanoparticles (e.g., in the form of a powder or a colloidal dispersion) and allowing the surface-modifying agent to react with the nanoparticles. Other useful surface-modification processes are described in U.S. Pat. No. 2,801,185 (Iler) and U.S. Pat. No. 4,522,958 (Das et al.), the disclosures of each of which are incorporated herein by reference.

Typically, the nanoparticles are inorganic. Examples of suitable inorganic nanoparticles include silica and metal oxide nanoparticles including zirconia, titania, ceria, alumina, iron oxide, vanadia, antimony oxide, tin oxide, alumina/silica, and combinations thereof. The nanoparticles have an average primary particle diameter less than about 100 nm, or no greater than about 50 nm, or from about 3 nm to about 50 nm, or from about 3 nm to about 20 nm, or even from about 5 nm to about 10 nm.

Useful surface-modified zirconia nanoparticles include a combination of oleic acid and acrylic acid adsorbed onto the surface of the particle.

Useful surface-modified silica nanoparticles include silica nanoparticles surface-modified with silane surface-modifying agents including, e.g., acryloyloxypropyl trimethoxysilane, 3-methacryloyloxypropyltrimethoxysilane, 3-mercaptopropyltrimethoxysilane, n-octyltrimethoxysilane, isooctyltrimethoxysilane, and combinations thereof. Silica nanoparticles can be treated with a number of surface-modifying agents including, e.g., alcohol, organosilane including, e.g., alkyltrichlorosilanes, trialkoxyarylsilanes, trialkoxy(alkyl)silanes, and combinations thereof and organotitanates and mixtures thereof.

The nanoparticles may be obtained in the form of a colloidal dispersion. Examples of useful commercially available unmodified silica starting materials include nano-sized colloidal silicas available under the product designations NALCO 1040, 1050, 1060, 2326, 2327, and 2329 colloidal silica, each of which is available from Nalco Chemical Co., Naperville, Ill.

Useful metal oxide colloidal dispersions include colloidal zirconium oxide, suitable examples of which are described in U.S. Pat. No. 5,037,579, the disclosure of which is incorporated herein by reference, and colloidal titanium oxide, useful examples of which are described in PCT Publication No. WO 00/06495 entitled, "Nanosize Metal Oxide Particles for Producing Transparent Metal Oxide Colloids and Ceramers," (Arney et al.) filed Jul. 30, 1998, the disclosure of which is incorporated herein by reference.

The surface-modified nanoparticles as used herein may be distinguished from materials such as fumed silica, pyrogenic silica, precipitated silica, etc. Such silica materials are known to those of skill in the art as being comprised of primary particles that are essentially irreversibly bonded together and from which it is not possible to straightforwardly extract individual primary particles.

Various methods may be employed to combine the surface-modified nanoparticles and the cold-water-soluble gelling agent. In one method, a dispersion of surface-modified nanoparticles and cold-water-soluble gelling agent are combined. Solvent present in the composition is then removed, leaving the surface-modified nanoparticles dispersed in the gelling agent. The solvent may be removed by evaporation including, e.g., distillation, rotary evaporation or oven drying. Optionally, for some colloidal dispersions, e.g., aqueous colloidal dispersions, prior to addition of the vehicle, a cosolvent (e.g., methoxy-2-propanol or N-methylpyrrolidone) may be added to the colloidal dispersion to assist removal of water. After the vehicle is added, the water and cosolvent are removed.

Another method for incorporating dispersions of surface-modified nanoparticles into a cold-water-soluble gelling agent includes drying the colloidal dispersion of surface-modified nanoparticles to a powder, followed by addition of the gelling agent or at least one component of the gelling agent into which the nanoparticles are to be dispersed. The drying step may be accomplished by conventional means such as oven drying or spray drying. The surface-modified nanoparticles preferably have a sufficient amount of surface groups to prevent irreversible agglomeration or irreversible aggregation upon drying. The drying time and the drying temperature is preferably minimized for nanoparticles having less than 100% surface coverage.

Dispersions of surface-modified nanoparticles can be added to the cold-water-soluble gelling agent in amounts sufficient to provide a composition capable of minimizing the formation of air bubbles or other irregularities upon hydration. Surface-modified nanoparticles may be present in the coating composition in varying amounts including, e.g., from about 0.00001% by dry weight to about 0.1% by dry weight, or from about 0.0001% by dry weight to about 0.01% by dry weight, based on the total weight of the coating composition. The surface-modified nanoparticles are typically dispersed throughout the coating composition, or dispersed homogeneously throughout the coating composition.

Figure 3:
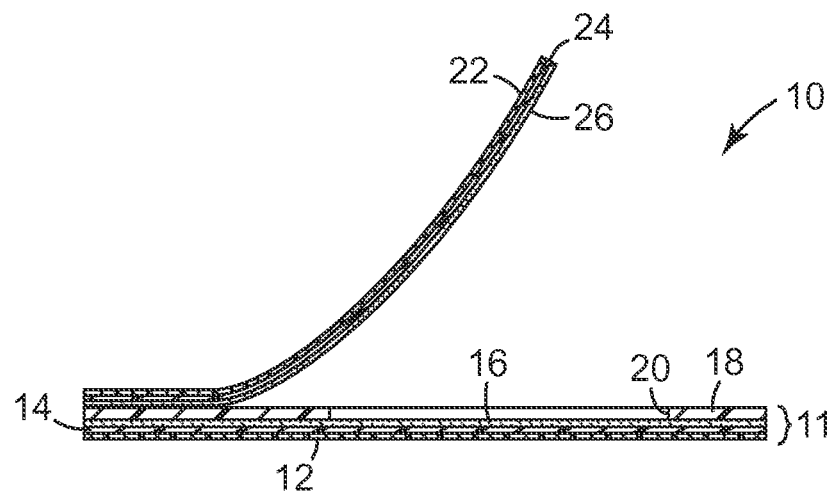
FIG. 3 is a cross sectional view of the device of FIG. 1.

The use of the devices of the present invention will be discussed with specific reference to the device of FIGS. 1 and 3. To use the device of FIGS. 1 and 3 as a pour plate, cover sheet 22 is pulled back and a predetermined quantity of water or an aqueous test sample is placed on substrate 12 of body member 11. The gelling agent and/or nutrients adhered to substrate 12 by adhesive 14 are quickly hydrated or dissolved and a nutrient gel is formed. Cover sheet 22 is then replaced over the substrate carefully, in order to minimize entrapment of air bubbles, and a weighted plate is placed on top temporarily to spread the sample completely. The device is then incubated for a predetermined period of time. Any bacterial colonies growing in the medium can be counted through the transparent cover film.

Embodiments

Item 1. A coating composition, comprising:
(a) a powdered cold-water-soluble gelling agent; and
(b) surface-modified nanoparticles disposed in the powdered cold-water-soluble gelling agent in a range from 0.00001 wt. % to about 0.1 wt. % of the coating composition, the surface-modified nanoparticles having an average primary particle diameter of less than about 100 nanometers.

Item 2. The coating composition of item 1, wherein said surface-modified nanoparticles comprise from 0.0001 wt. % to 0.01 wt. % of the coating composition.

Item 3. The coating composition of item 1, wherein the average primary particle diameter is less than 50 nanometers.

Item 4. The coating composition of item 1, wherein the average primary particle diameter is less than 20 nanometers.

Item 5. The coating composition of item 1, wherein the average primary particle diameter is in a range from about 3 nanometers to about 20 nanometers.

Item 6. The coating composition of item 1, wherein the average primary particle diameter is in a range from about 3 nanometers to about 10 nanometers.

Item 7. The coating composition of item 1, wherein the surface-modified nanoparticles comprise nanoparticles selected from the group consisting of silica, titania, alumina, zirconia, vanadia, ceria, iron oxide, antimony oxide, tin oxide, calcium phosphate, hydroxyapatite, aluminum/silica and combinations thereof.

Item 8. The coating composition of item 1, wherein the surface-modified nanoparticles comprise surface groups selected from the group consisting of hydrophobic groups, hydrophilic groups and combinations thereof.

Item 9. The coating composition of item 1, wherein the surface-modified nanoparticles comprise surface groups derived from an agent selected from the group consisting of silane groups, organic acid groups, organic base groups and combinations thereof.

Item 10. The coating composition of item 1, wherein the surface-modified nanoparticles comprise organosilyl surface groups derived from an agent selected from the group consisting of alkylsilane, arylsilane, alkoxysilane and combinations thereof.

Item 11. The coating composition of item 1, wherein the powdered cold-water-soluble gelling agent comprises a mixture of locust bean gum and xanthan gum.

Item 12. The coating composition of item 11, wherein the locust bean gum and xanthan gum are present in a ratio of about 1:1.

Item 13. A coated film, comprising:
a transparent film having an adhesive layer on a major surface thereof, wherein the adhesive is non-inhibitory to the growth of microorganisms; and
the coating composition of item 1 adhered to the adhesive layer.

Item 14. The coated film of item 13, wherein the transparent film is selected from the group consisting of polyester, polyethylene, polypropylene, polystyrene and silicone.

Item 15. The coated film of item 13, wherein the transparent film is biaxially oriented polypropylene.

Item 16. The coated film of item 13, wherein the transparent film has a thickness in a range from about 2 micrometers to about 38 micrometers.

Item 17. The coated film of item 13, wherein the adhesive is a pressure-sensitive adhesive.

Item 18. The coated film of item 13, wherein the adhesive is substantially transparent when wetted with water.

Item 19. A device for growing microorganisms, comprising:
a body member comprising a substrate having upper and lower surfaces, wherein the substrate is self-supporting and water-proof;
a layer of adhesive coated on the upper surface of the substrate, wherein the adhesive is non-inhibitory to the growth of microorganisms;
a cold-water-soluble powder adhered uniformly to the layer of adhesive, the cold-water-soluble powder comprising at least a single ingredient selected from the group consisting of gelling agent, one or more nutrients for growing microorganisms, and a mixture thereof;
a cover sheet comprising the coated film of item 13, wherein the major surface having the coating composition of item 1 faces the upper surface of the substrate, and wherein the cover sheet is releasably adhered to at least a portion of the body member.

Item 20. The device of item 19, further comprising a hydrophobic spacer element adhered to the upper surface of the substrate, forming side walls to retain a predetermined amount of liquid in contact with the substrate.

Item 21. The device of item 20, wherein the hydrophobic spacer element comprises a hydrophobic foam sheet defining an aperture therein.

Item 22. The device of item 21, wherein the hydrophobic foam sheet comprises polystyrene or polyethylene.

Item 23. The device of item 19, wherein the substrate is a film selected from the group consisting of polyester, polyethylene, polypropylene, and polystyrene.

Item 24. The device of item 23, wherein the film has a thickness in a range from about 2 micrometers to about 38 micrometers.

Item 25. The device of item 19, wherein the substrate has a grid pattern printed thereon.

Item 26. The device of item 19, wherein the gelling agent is selected from the group consisting of xanthan gum, guar gum, carboxymethyl cellulose, hydroxyethyl cellulose, and algin.

Item 27. The device of item 26, wherein the gelling agent is guar gum, xanthan gum, or mixtures thereof.

Item 28. The device of item 19, wherein the adhesive layer on a major surface of the transparent film is a pressure-sensitive adhesive.

Item 29. The device of item 19, wherein the adhesive layer on a major surface of the transparent film is substantially transparent when wetted with water.

Item 30. A method of detecting the presence or absence of a microorganism, the method comprising:
providing the device of any of items 19 to 29;
contacting a sample suspected of including the microorganism onto the cold-water-soluble powder; and
detecting the presence or absence of the microorganism in the sample.

Embodiments of the disclosure may be further illustrated by reference to the following non-limiting examples. All concentrations are expressed as percent by weight (wt. %) unless otherwise indicated.

EXAMPLES

Example 1

Powdered Coating Compositions Including Surface-Modified Nanoparticles

Silica nanoparticles surface-modified with isooctyltrimethoxysilane were prepared as follows: 7.65 g isooctyltrimethoxysilane (obtained from Gelest, Tullytown, Pa.), 0.79 g methyltrimethoxysilane (obtained from Gelest), 90 g ethanol, 23 g of methanol and 100 g of 16 wt. % solids colloidal silica (obtained from Nalco Co., Naperville, Ill., under the trade designation "NALCO 2326") were combined in a three-neck flask equipped with a water cooled condenser and a mechanical stirrer. The mixture was stirred at 80° C. overnight. The mixture was then dried in a flow through oven at 150° C. to produce the surface-modified nanoparticles as a white particulate solid.

A 500 g portion of NF Grade xanthan gum powder (obtained from Spectrum Chemical Mfg. Corp., Gardena, Calif.) was mixed together with a 500 g portion of FCC grade locust bean gum powder (Spectrum Chemical Mfg. Corp.) to give a gum powder mixture, and to a portion of this gum powder mixture was added 1.0 wt. % of the above surface-modified nanoparticles as a solid, followed by mixing on a rotator for approximately 5 minutes to give the coating composition as a white powder. Dilutions of the powdered coating composition were made with additional portions of the gum powder mixture, in order to give a group of powdered coating compositions covering a range of concentrations (wt. %) of surface-modified nanoparticles in the powder coating composition, as shown in Table 1.

TABLE 1

Powdered Coating Composition including Surface-modified Nanoparticles

| Powdered Coating Composition | Surface-modified nanoparticles, wt. % |
|---|---|
| Powder 1 (Control) | 0 |
| Powder 2 | 1.0 |
| Powder 3 | 0.1 |
| Powder 4 | 0.01 |
| Powder 5 | 0.001 |
| Powder 6 | 0.0001 |
| Powder 7 | 0.00001 |

Example 2

Transparent Films Coated with Powder Coated Compositions Including Surface-Modified Nanoparticles The powdered coating compositions of Example 1 were each independently coated onto a corresponding sheet of transparent polyolefin film having a silicone pressure-sensitive adhesive coated on a major surface thereof (obtained from 3M Company, St. Paul, Minn., under the trade designation "ADVANCED POLYOLEFIN DIAGNOSTIC TAPE, CATALOG #9795R"). An excess amount of the powdered coating composition was sprinkled onto the surface of the adhesive, and non-adhered powdered coating composition was then the sheet of polyolefin film was lightly tapped by hand to remove excess powdered coating composition, giving the powder coated films listed in Table 2.

TABLE 2

Powder Coated Transparent Films

| Powder Coated Transparent Films | Wt. % of surface-modified nanoparticles in the coating composition |
|---|---|
| Coated Film 1 (Control) | 0 |
| Coated Film 2 | 1.0 |
| Coated Film 3 | 0.1 |
| Coated Film 4 | 0.01 |
| Coated Film 5 | 0.001 |
| Coated Film 6 | 0.0001 |
| Coated Film 7 | 0.00001 |

Example 3

Devices (Plates) for Growing Microorganisms, Including Powder Coated Films as a Cover Sheet A nutrient mixture was prepared by mixing 22.8 wt. % of pancreatic digest of casein, 15.9 wt. % of yeast extract, 45.5 wt. % of sodium pyruvate, 4.1 wt. % of dextrose, 9 wt. % of potassium phosphate, dibasic, and 2.8 wt. % of potassium phosphate, monobasic. A nutrient broth was prepared by mixing 500 milliliters of reverse osmosis treated water with 14.78 grams of the above nutrient mixture in a beaker using an air motor mixer. Then 5 grams of locust bean gum (commercially available from CP Kelco, Atlanta, Ga.) was mixed with the broth in small increments to avoid clumping, followed by mixing thoroughly for several minutes. The beaker was then covered with foil and the mixture was heated to 80° C. and mixed for about 6 minutes. The mixture was allowed to cool for about ten minutes while mixing and then was poured into a sterilized beaker, which was then covered with a plastic bag and placed in a refrigerator to aid cooling. Before coating, the broth was stirred carefully with a spatula to avoid forming air bubbles. A sheet of 4 mil (102 micrometers) thick polyethylene terephthalate film (obtained from DuPont Teijin Films, Hopewell, Va., under the trade designation "MELINEX") was knife coated with the broth mixture to a dry coating weight of about 150 mg per 24 square inches (about 1 mg per square centimeter). The broth-coated film was dried in an oven with a temperature set at 210° C. for about 5 minutes. The dried broth-coated film measured about 8 inches by about 72 inches (about 20 centimeters by about 183 centimeters).

A laminate was prepared by laminating a 7.5 inch (19 centimeters) wide sheet of a 4 mil (102 micrometers) thick polystyrene foam dam to a pressure-sensitive adhesive transfer tape on a liner. Circular discs measuring 5 centimeters in diameter were die-cut from the laminate to form a circular cut-out disc centered within a 3 inch (7.6 centimeter) square on the laminate, and the discs were removed. The liner was removed from the remaining laminate and the adhesive-coated surface of the polystyrene foam was adhered to the broth coated film, to provide a device body member 11 having a broth-coated self-supporting substrate and a hydrophobic spacer element (i.e., "foam dam") adhered to the broth-coated surface of the supporting substrate. Rectangular plates measuring 3 inches by 3.5 inches (7.6 centimeter by 8.9 centimeter) were cut from the laminate, with the circular cut-out opening centered across the 3 inch (7.6 centimeter) width. A cover sheet was added to each of the individual rectangular plates by attaching the coated side of one of the coated films of Example 2 to one end of an exposed surface of the polystyrene foam layer, using a piece of double sided pressure-sensitive adhesive tape as a hinge, to give plate devices of the construction showing in FIG. 1 and FIG. 3. The plate devices are listed in subsequent tables as Plates 1-7, according to the wt. % of surface-modified nanoparticles in the coating on the cover sheet.

Individual plates 1-7 listed in Table 3 (with cover sheet coatings having the indicated wt. % of surface-modified nanoparticles ("SMPs") in the cover sheet coatings) were hydrated by peeling back the cover sheet, adding a 1 milliliter (mL) sample of water into the well defined by the foam dam, laying the cover sheet back down onto the surface of the foam dam, and incubating the plates at 30° C. overnight, to simulate normal use of the plates. The plates were analyzed for % transmittance, % haze and % clarity according ASTM D1003.23663-1 (i.e., ASTM D1003-07e1), giving the results listed in Table 3.

TABLE 3

% Transmittance, % Haze and % Clarity for Hydrated Plates 1-7.

| Plate Number | Wt % SMPs in cover sheet coating | % Transmittance | % Haze | % Clarity |
|---|---|---|---|---|
| Plate 1 | none | 87.1 | 19.9 | 74.2 |
| Plate 2 | 1.0 | 88.0 | 27.6 | 78.5 |
| Plate 3 | 0.1 | 89.9 | 22.0 | 71.4 |
| Plate 4 | 0.01 | 90.0 | 17.4 | 71.9 |
| Plate 5 | 0.001 | 88.7 | 24.2 | 75.5 |
| Plate 6 | 0.0001 | 89.5 | 16.5 | 75.2 |
| Plate 7 | 0.00001 | 90.4 | 17.5 | 70.6 |

Plates 1-7 were also imaged using a UV imager (obtained from Cell Biosciences, Santa Clara, Calif., under the trade designation "ALPHAIMAGER"), with peak emission at 365 nm and an exposure time of 2 seconds. UV imaging was performed approximately 30 minutes after removing the plates from the incubator. UV images of the plates 2-5 (i.e., those plates having from 0.001 wt. % to 1.0 wt. % of the surface-modified nanoparticles in the coating on the cover sheet) showed a more uniform background appearance, and smaller bubbles, than UV images of the other plates in Table 3.

Example 4

Viability of Bacteria in Devices of the Description

Bacterial cultures were prepared by inoculating pure cultures obtained from American Tissue Culture Collection (ATCC) into Tryptic Soy Broth and incubating overnight. The organisms cultured were *Echerichia coli* (*E. coli*; ATCC #11229), *Pseudomonas* (Ps8; ATCC #51821), *Microbacterium esteraromaticum* (MC3; ATCC #51822) and *Acenitobacter lwoffii* (MC7 ATCC #51819). *E. coli* was incubated at 37° C. and the other organisms were incubated at 30° C.

The overnight cultures were diluted to an A600 (i.e., an absorbance measured at 600 nm to an optical density of 0.6 absorbance units in Butterfield's Reagent). Dilutions with Butterfield's Reagent were performed to about 100 cells/mL. A dye, 2,3,5-tetraphenyl tetrazolium chloride (obtained from Sigma, St. Louis, Mo.), was added to the 100 cells/mL dilution at a concentration of 20 μg/mL and plates 1, 4, 5 and 6 prepared as in Example 3 were inoculated with 1 milliliter of this dilution. For comparison, a count plate (obtained from 3M Company, under the trade designation "3M PETRIFILM AEROBIC COUNT PLATE", and designated as "PFAC" in Table 4) was also inoculated. A duplicate set of plates was prepared in the same way. The plates were incubated overnight at 37° C. for *E. coli*, and at 30° C. for the other organisms. Photos of the plates were taken under UV light using the ALPHAIMAGER, using a dark background, and the number of colony forming units (CFUs) was counted using the ALPHAIMAGER Analysis function. CFU counts are shown in Table 4 as an average number of CFUs for the two sets of plates.

TABLE 4

| Plate Number | Organism | Average Count of CFUs (Std. Dev.) | Wt. % of surface-modified nanoparticles in cover sheet coating |
|---|---|---|---|
| 1 (Control) | MC7 | 94.5 (6.4) | 0 |
| 4 | MC7 | 86.5 (2.1) | 0.01 |
| 5 | MC7 | 79.5 (7.8) | 0.001 |
| 6 | MC7 | 86.5 (9.2) | 0.0001 |
| PFAC | MC3 | 95.0 (7.1) | 0 |
| 1 (Control) | MC3 | 111.5 (9.2) | 0 |
| 4 | MC3 | 119.5 (6.4) | 0.01 |
| 5 | MC3 | 119.5 (2.1) | 0.001 |
| 6 | MC3 | 124.5 (2.1) | 0.0001 |
| PFAC | MC3 | 118.5 (5.0) | 0 |
| 1 (Control) | Ps8 | 108.0 (4.2) | 0 |
| 4 | Ps8 | 110.0 (0.0) | 0.01 |
| 5 | Ps8 | 109.0 (9.9) | 0.001 |
| 6 | Ps8 | 112.5 (0.7) | 0.0001 |
| PFAC | Ps8 | 112.5 (7.8) | 0 |
| 1 (Control) | *E. coli* | 137.5 (10.6) | 0 |
| 4 | *E. coli* | 127.0 (5.7) | 0.01 |
| 5 | *E. coli* | 131.5 (0.7) | 0.001 |
| 6 | *E. coli* | 131.0 (0.0) | 0.0001 |
| PFAC | *E. coli* | 133.5 (12) | 0 |

The tests and test results described above are intended solely to be illustrative, rather than predictive, and variations in the testing procedure can be expected to yield different results. All quantitative values in the Examples section are understood to be approximate in view of the commonly known tolerances involved in the procedures used. The foregoing detailed description and examples have been given for clarity of understanding only. No unnecessary limitations are to be understood therefrom.

What is claimed is:

1. A device for growing microorganisms, comprising:
a body member comprising a substrate having upper and lower surfaces, wherein the substrate is self-supporting and water-proof;
a first layer of adhesive coated on the upper surface of the substrate, wherein the first layer of adhesive is non-inhibitory to the growth of microorganisms;
a cold-water-soluble powder adhered uniformly to the first layer of adhesive, the cold-water-soluble powder comprising at least a single ingredient selected from the group consisting of gelling agent, one or more nutrients for growing microorganisms, and a mixture thereof;
a cover sheet releasably adhered to at least a portion of the body member, wherein the cover sheet comprises (1) a transparent film and (2) a second layer of adhesive disposed on the transparent film, wherein the second layer of adhesive is non-inhibitory to the growth of microorganisms and (3) a coating composition adhered to the second layer of adhesive, wherein the coating composition faces the upper surface of the substrate and wherein the coating composition comprises
(a) a powdered cold-water-soluble gelling agent; and
(b) surface-modified nanoparticles disposed in the powdered cold-water-soluble gelling agent in a range from 0.00001 wt. % to about 0.1 wt. % of the coating composition, the surface-modified nanoparticles having an average primary particle diameter of less than about 100 nanometers.

2. The device of claim 1, further comprising a hydrophobic spacer element adhered to the upper surface of the substrate, forming side walls to retain a predetermined amount of liquid in contact with the substrate.

3. The device of claim 2, wherein the hydrophobic spacer element comprises a hydrophobic foam sheet defining an aperture therein.

4. The device of claim 3, wherein the hydrophobic foam sheet comprises polystyrene or polyethylene.

5. The device of claim 1, wherein the substrate is a film selected from the group consisting of polyester, polyethylene, polypropylene, and polystyrene.

6. The device of claim 5, wherein the film has a thickness in a range from about 2 micrometers to about 38 micrometers.

7. The device of claim 1, wherein the gelling agent is selected from the group consisting of xanthan gum, guar gum, carboxymethyl cellulose, hydroxyethyl cellulose, and algin.

8. The device of claim 7, wherein the gelling agent is guar gum, xanthan gum, or mixtures thereof.

9. The device of claim 1, wherein the second layer of adhesive is a pressure-sensitive adhesive.

10. The device of claim 1, wherein the second layer of adhesive is substantially transparent when wetted with water.

11. The device of claim 1, wherein the surface-modified nanoparticles comprise nanoparticles selected from the group consisting of silica, titania, alumina, zirconia, vanadia, ceria, iron oxide, antimony oxide, tin oxide, calcium phosphate, hydroxyapatite, aluminum/silica and combinations thereof.

12. The device of claim 1, wherein the surface-modified nanoparticles comprise organosilyl surface groups derived from an agent selected from the group consisting of alkylsilane, arylsilane, alkoxysilane and combinations thereof.

\* \* \* \* \*